US011896259B2

(12) United States Patent
Hatta et al.

(10) Patent No.: US 11,896,259 B2

(45) Date of Patent: Feb. 13, 2024

(54) ATHERECTOMY DEVICE AND METHOD

(71) Applicant: TERUMO KABUSHIKI KAISHA, Tokyo (JP)

(72) Inventors: Tomonori Hatta, Cupertino, CA (US); Kousuke Nishio, Machida (JP); Taiga Nakano, Sunnyvale, CA (US); Junichi Kobayashi, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 67 days.

(21) Appl. No.: 16/693,822

(22) Filed: Nov. 25, 2019

(65) Prior Publication Data

US 2020/0155195 A1 May 21, 2020

Related U.S. Application Data

(63) Continuation of application No. PCT/JP2018/020380, filed on May 28, 2018.

(Continued)

(51) Int. Cl.

*A61B 17/3207* (2006.01)

*A61B 17/00* (2006.01)

(52) U.S. Cl.

CPC ................ *A61B 17/320758* (2013.01); *A61B 2017/00309* (2013.01); *A61B 2017/00314* (2013.01);

(Continued)

(58) Field of Classification Search

CPC .......... A61B 17/320758; A61B 2017/320733; A61B 2017/00314; A61B 2017/00323;

(Continued)

(56) References Cited

U.S. PATENT DOCUMENTS

2002/0007190 A1* 1/2002 Wulfman ....... A61B 17/320758 606/167

2006/0015126 A1* 1/2006 Sher .............. A61B 17/320758 606/159

(Continued)

FOREIGN PATENT DOCUMENTS

| | | | |
|---|---|---|---|
| WO | 9923958 | A1 | 5/1999 |
| WO | 2014123874 | A1 | 8/2014 |
| WO | 2018051894 | A1 | 3/2018 |

OTHER PUBLICATIONS

International Search Report (PCT/ISA/210) dated Sep. 28, 2018, by the Japanese Patent Office as the International Searching Authority for International Application No. PCT/JP2018/020380.

(Continued)

*Primary Examiner* — Sarah A Long

*Assistant Examiner* — Raihan R Khandker

(74) *Attorney, Agent, or Firm* — BUCHANAN INGERSOLL & ROONEY PC

(57) ABSTRACT

A medical device is disclosed, the medical device includes an outer tubular member made from one or more rigid materials having a first bend element including a distal end portion of the outer tubular member and a second bend element proximal to the first bend element in a natural state; and a treatment member on the distal end portion configured to grind a substance inside a body lumen, and wherein an outer diameter of the treatment member is larger than an outer diameter of the outer tubular member, and a difference between the outer diameter of the treatment member and the outer diameter of the outer tubular member is less than a thickness of a blood vessel wall.

22 Claims, 14 Drawing Sheets

Related U.S. Application Data

(60) Provisional application No. 62/512,487, filed on May 30, 2017.

(52) U.S. Cl.
CPC ............... *A61B 2017/00398* (2013.01); *A61B 2017/00734* (2013.01); *A61B 2017/00867* (2013.01); *A61B 2217/005* (2013.01)

(58) Field of Classification Search
CPC .......... A61B 2017/00327; A61B 2017/00331; A61B 2017/00309; A61B 2017/00867; A61B 17/32
See application file for complete search history.

(56) References Cited

U.S. PATENT DOCUMENTS

2009/0234378 A1* 9/2009 Escudero .............. A61M 25/09 606/180
2012/0143175 A1* 6/2012 Hermann ........... A61B 17/1631 606/1
2013/0096587 A1* 4/2013 Smith ............ A61B 17/320758 606/159
2015/0141816 A1* 5/2015 Gupta .............. A61B 17/32002 600/427
2016/0235434 A1 8/2016 Smith et al.
2017/0065295 A1 3/2017 Patel et al.
2019/0069949 A1* 3/2019 Vrba ...................... A61B 18/02

OTHER PUBLICATIONS

Written Opinion (PCT/ISA/237) dated Sep. 28, 2018, by the Japanese Patent Office as the International Searching Authority for International Application No. PCT/JP2018/020380.

* cited by examiner 102
160
154
184
176
180
140
138
136
119
142
143
144

102
140
168
164
162
154
116
117
114
115
136
142
143
144
138
162
160
152
170
150 d: Diameter of first tubular member
h: Inner diameter of a target blood vessel lumen
θ1: Degree of first bend element
θ2: Degree of second bend element
l: Length between first bend element and second bend element

- $l > h - d$
- $\theta 2 > \tan^{-1} l / (h - d)$
- $\theta 1 = \theta 2$ (ideal)

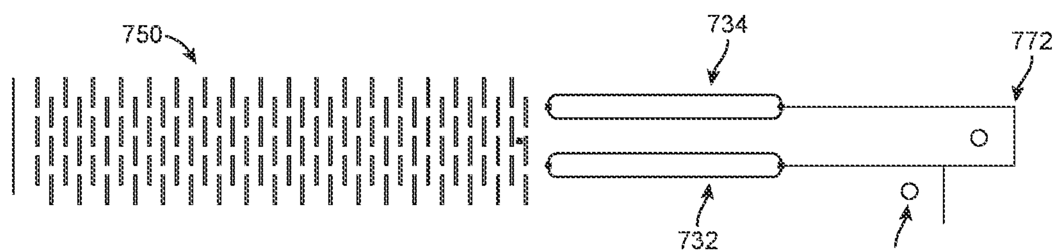
FIG. 13A
772
770
FIG. 13B
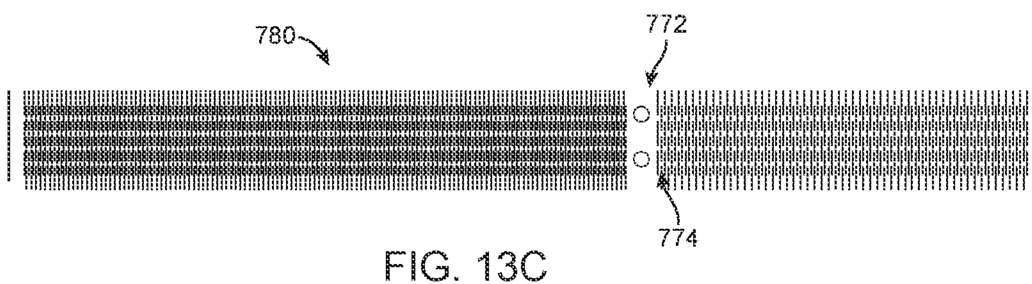
FIG. 13C

ATHERECTOMY DEVICE AND METHOD

CROSS-REFERENCES TO RELATED APPLICATIONS

This application is a continuation of International Application No. PCT/JP2018/020380 filed on May 28, 2018, which claims priority to U.S. Patent Application Ser. No. 62/512,487 filed on May 30, 2017, the entire content of both of which is incorporated herein by reference.

FIELD OF THE DISCLOSURE

The present disclosure generally relates to atherectomy devices and methods for removing substances from a living body. More specifically, the present disclosure involves positioning a rotatable treatment member in a living body with a pre-bent portion or manually bendable portion and cutting the substance in the living body through rotation of the treatment member.

BACKGROUND DISCUSSION

Medical devices are used to remove substances from a living body. As an example, an atherectomy device is used to remove arteriosclerosis from a blood vessel. The atherectomy device is typically configured to be positioned in the living body adjacent the substance to be cut and then the treatment part of the device is then rotated to cut the substance. The debris resulting from this cutting procedure is then removed from the living body. The removal of the cut-away debris can be accomplished by way of a gateway lumen passing through the atherectomy device.

Experience has shown that these known devices and methods can result in distal embolization. That is, some of the debris can create an obstruction or blockage resulting in slow flow or no flow in the peripheral vessel. When this occurs, physicians must aspirate the peripheral vessel to remove the debris forming the distal embolization. In very severe cases, it may be necessary to perform amputation.

Proposals have been made to address concerns about distal embolization. For example, some atherectomy devices are provided with an aspiration function for removing the debris by way of an aspiration port. However, these solutions have not been found to be particularly satisfactory. In some instances, choking of the aspiration port occurs, thus inhibiting or preventing a continuous aspiration of the desired region.

The atherectomy procedure for cutting substance from a living body lumen (removing arteriosclerosis from a blood vessel) typically involves the use of two different guidewires. A first coated guidewire is used to deliver the atherectomy device to the stenotic region or treatment area. After the atherectomy device is located at the desired position, the coated guidewire is removed and a second different guidewire is inserted into the atherectomy device. One way in which the second guidewire differs from the first is that the second guidewire is not coated. This second non-coated guidewire is used during operation of the atherectomy device when the treatment part is rotated at a high speed.

The reason two different guidewires are used is that the coated first guidewire is a preferred guidewire for guiding and delivering the atherectomy device to the treatment area. However, the coating on this first guidewire tends to become abraded or damaged during rotation of the treatment part. The abrasion of the rotating treatment part against the coated guidewire can produce coating fragments that may cause distal embolization.

SUMMARY

In accordance with an aspect, a medical device is disclosed, the medical device includes an outer tubular member made from one or more rigid materials having a first bend element including a distal end portion of the outer tubular member and a second bend element proximal to the first bend element in a natural state; and a treatment member on the distal end portion configured to grind a substance inside a body lumen.

In accordance with another aspect, a medical device is disclosed, the medical device includes an outer tubular member made from one or more rigid materials having a first bend element including a distal end portion of the outer tubular member and a second bend element proximal to the first bend element in a natural state; a treatment member on the distal end portion configured to grind a substance inside a body lumen; and wherein an outer diameter of the treatment member is larger than an outer diameter of the outer tubular member, and a difference between the outer diameter of the treatment member and the outer diameter of the outer tubular member is less than a thickness of a blood vessel wall.

In accordance with an aspect, a medical device is disclosed, the medical device includes an outer tubular member made from one or more rigid materials having a first bend element including a distal end portion of the outer tubular member and a second bend element proximal to the first bend element in a natural state; a portion of the outer tubular member located proximally of the first bend element is formed with a plurality of slits extending to a circumferential direction, each of the plurality of slits being perpendicular to a shaft center of the outer tubular member and formed with a length less than 360 degrees to the circumferential direction of the outer tubular member; a portion of the outer tubular member located distally of the second bend not cut by the slits to the circumferential direction; the first bend element of the outer tubular member being formed with at least one joint aligned in an axial direction, the joint having a concave part and a convex part fitted with each other in a relatively rotatable manner; and a treatment member on the distal end portion configured to grind a substance inside a body lumen.

In accordance with another aspect, a method is disclosed comprising: introducing a treatment member on a distal end portion of an outer tubular member into a living body and positioning the treatment member adjacent to a substance in the living body to be ground, the medical device includes an outer tubular member made from one or more rigid materials having a first bend element including a distal end portion of the outer tubular member and a second bend element proximal to the first bend element in a natural state; rotating the treatment member while the treatment member is positioned adjacent to the substance to be ground in the living body to grind the substance; and shearing debris resulting from the grinding of the substance to reduce a size of the debris.

BRIEF DESCRIPTION OF THE DRAWINGS

FIG. 13A is an illustration of a portion of a medical device having a manual bending member in accordance with another exemplary embodiment.

FIG. 13B is an illustration of a portion of a medical device having a manual bending member in accordance with another exemplary embodiment.

FIG. 13C is an illustration of a portion of a medical device having a manual bending member in accordance with another exemplary embodiment.

DETAILED DESCRIPTION

Figure 1:
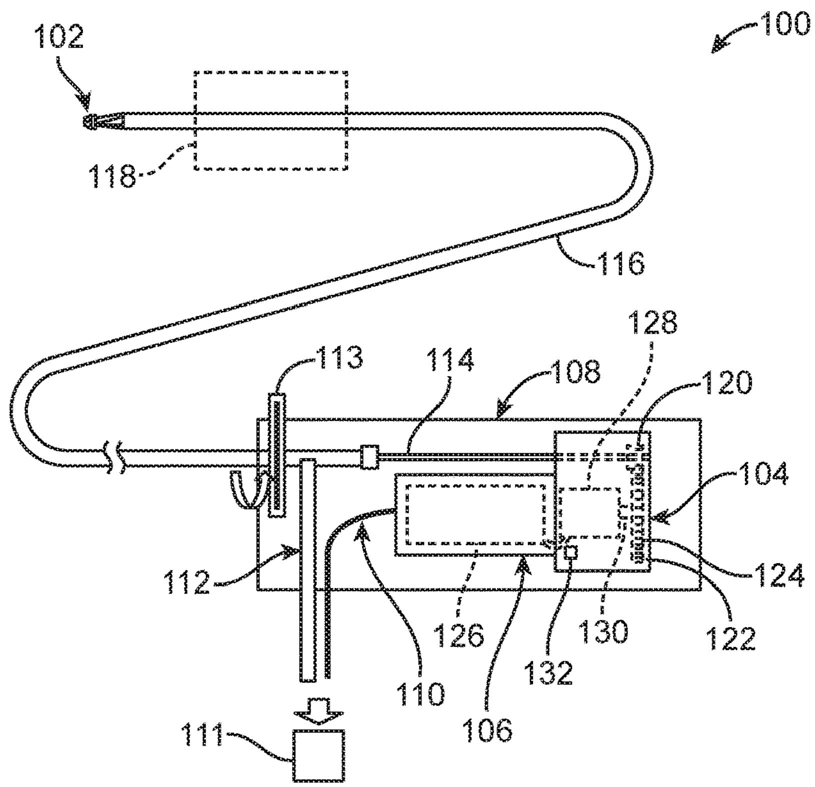
FIG. 1 is a schematic view of the medical device according to one embodiment.

Hereinafter, embodiments of the present disclosure will be described with reference to the drawings. In order to facilitate description, dimensional ratios in the drawings are exaggerated, and thus are different from actual ratios in some cases.

FIG. 1 schematically illustrates one embodiment of the medical device representing an example of the inventive medical device disclosed here. This disclosed medical device is configured to grind a substance in a body lumen such as arteriosclerosis in a blood vessel. The terms "grind" and "grinding" as used here are not limited to any particular operation or manner of acting on the substance, and include operations such as scraping, abrading, ablating, macerating, grinding and otherwise breaking down desired substance or material into particles or other smaller units of material to facilitate removal from the living body (e.g., blood vessel).

Figure 2A:
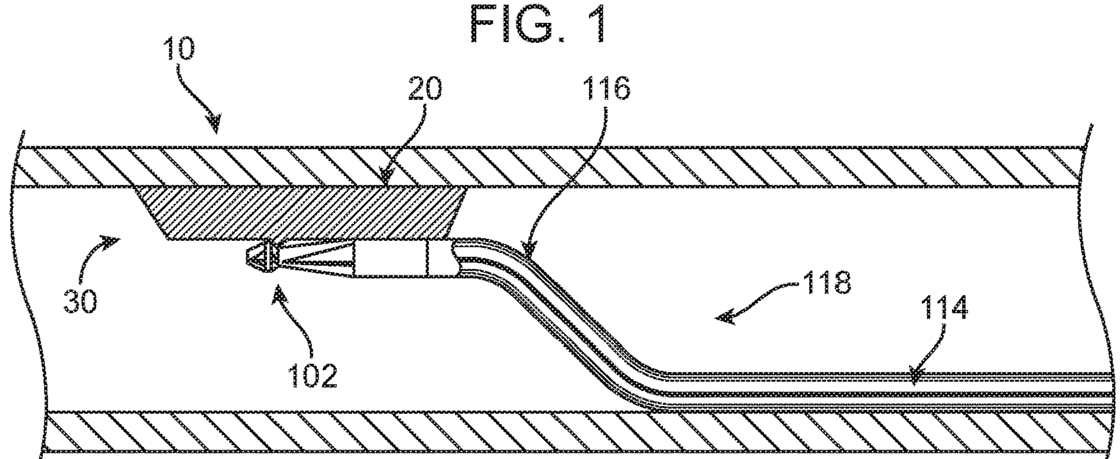
FIGS. 2A and 2B are cross-sectional views of the distal portion of the medical device, including the treatment member having a pre-bending portion or manual bending portion, positioned in a blood vessel to grind-away or cut-away a substance in the blood vessel.
Figure 2B:
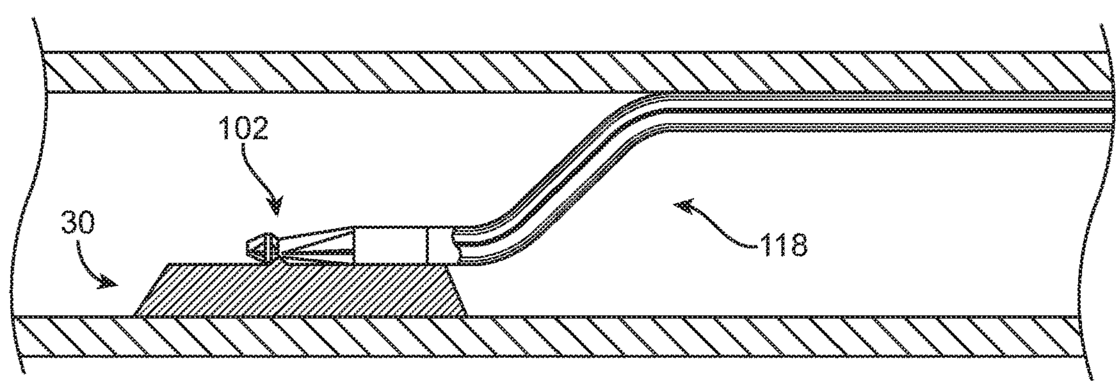

The medical device 100 shown in FIG. 1 can be used to grind a stenosis 30 such as shown in FIGS. 2A, 2B from a blood vessel 10, which stenosis can be constituted by a thrombus, calcified lesion, etc. Referring initially to FIG. 1, the medical device 100 may include a treatment member 102 and an operation unit 104 configured to transmit a rotation driving force to the treatment member 102 to rotate the treatment member 102. The operation unit 104 may be housed in a handle 108.

The operation unit 104 includes a motor 28 that produces a rotational output force. The operation unit 104 also includes a drive mechanism section 122 for transmitting or applying the rotational output shaft of the motor 28 to the drive shaft 114. The drive mechanism section 122 includes a drive gear 124 and a driven gear 120 that mesh with one another so that rotation of the drive gear 124 results in rotation of the driven gear 120. The motor 128 serves as a driving source and includes a rotatable motor shaft 130 to which the drive gear 124 is fixed so that the motor shaft 130 and the drive gear 124 rotate together as a unit. Operation of the motor 128 causes rotation of the motor shaft 130 which in turn results in rotation of the drive gear 124. The proximal end of the drive shaft 114 may be fixed to the driven gear 120 so that the drive shaft 114 and the driven gear 120 rotate together as a unit. Thus, the operation of the motor 128 and the rotation of the motor shaft 130 is transmitted to the treatment member 102 by way of the drive gear 124, the driven gear 120 and the drive shaft 114. A power supply section 106 that includes a battery 126 may be provided in the handle 108 and connected to the motor 128 to supply power to the motor 128. A power cable 110 may be connected to the battery 126 to supply power. FIG. 1 also shows that the medical device 100 may be provided with an aspiration tube 112 to remove (i.e., draw-away or suck-away) debris resulting the grinding of the substance 30.

The drive shaft 114 may be comprised of a tubular drive shaft that is hollow so that a central lumen extends throughout the entire axial extent of the drive shaft 114. The drive shaft 114 may preferably be flexible, but also well suited to transmitting the rotational output of the motor unit from the proximal end of the drive shaft 114 to the distal end of the drive shaft 114 at which the treatment member 102 is located. The drive shaft 114 may be any desired construction. For example, the drive shaft 114 may be constituted by a multi-layer structure. As an example, the drive shaft 114 may be configured as a multi-layered coiled tube made from, for example, a polyolefin such as polyethylene or polypropylene, polyamides, polyesters such as polyethylene terephthalate, fluorine series such as PTFE Polymer, PEEK, polyimide, or combinations thereof. The tubular drive shaft can also be provided with reinforcement. The size of the drive shaft may be appropriately selected. Examples of an appropriate size include an inner diameter of 0.40 mm-1.40 mm and an outer diameter of 0.6 mm-1.6 mm.

The drive shaft 114 is preferably a tubular drive shaft as mentioned above so that the drive shaft includes a lumen defining a guidewire-receiving passage. The guidewire passes through the lumen in the drive shaft and allows the drive shaft 114 together with the treatment member 102 to be navigated through the living body (e.g., the lumen of a blood vessel) to position the treatment member 102 at the desired place adjacent substance to be ground.

The drive shaft 114 may be housed in a tubular outer sheath 116. The outer sheath 116 may be a tubular body that accommodates the drive shaft 114 so that the drive shaft 114 is rotatable and axially movable relative to the outer sheath 116 and in the outer sheath 116. The material forming the outer sheath 116 is not limited to a particular material. By way of example, the outer sheath 116 may be made of polyethylene, polypropylene, polyolefin such as polyethylene terephthalate, polyester such as polyamide terephthalate, fluorine-based polymers such as PTFE, PEEK, polyimide and the like.

The operation of the motor 128 can be controlled by way of a switch 132. Operating or turning on the switch 132 causes the motor 128 to operate and rotate the motor shaft 130. As a result, the drive gear 124 rotates and in turn rotates the driven gear 120 which meshes with the drive gear 124. The rotation of the driven gear 120 results in rotation of the drive shaft 114 and ultimately rotation of the treatment member 102.

FIGS. 2A and 2B shows a state of grinding a stenosis 30 in a blood vessel 10 using the medical device 100 according to this embodiment. As shown in FIGS. 2A and 2B, when grinding the structure 30 on a vessel wall 20 of the blood vessel 10. Next, when the drive shaft 114 is rotated, the rolling structure 110 rotates and the third grinding part 118 and the first grinding part 123 rotate the inside of the living body lumen of the stenosis 30 can be ground. At this time, the diameter of the bottom portion 127 of the constricted portion 126 becomes the first diameter. The diameter of the annular portion 112 (see FIG. 3), and the diameter of the second annular portion 111 (see FIG. 3), it is possible to prevent the first grinding part 123 from coming into contact with the living tissue such as a normal blood vessel, and relatively high safety can be secured.

As shown in FIGS. 2A and 2B, the bending section 118 may be provided in the tubular outer sheath 116 and the drive shaft 114. This bending section 118 may be provided at an intermediate point along the length of the drive shaft 114 and the outer sheath 116. In this bending section 118, the outer sheath 116 and the drive shaft 114 are bent such as illustrated in FIGS. 2A and 2B. This allows the treatment unit 102 to be manipulated in a way that allows grinding of the stenosis 30 located in a blood vessel 20. That is, as the drive shaft 114 is rotated by operation of the motor 128, the treatment member 102 traces a movement path this circular or annular, as opposed to rotating about the central axis of the drive shaft 114. FIGS. 2A and 2B also illustrate that, during operation of the medical device while the treatment member 102 is positioned in the living body (blood vessel) and is being rotated, the distal end portion of the treatment member 102 is positioned distally beyond the distal-most end of the outer sheath 116.

Figure 3:
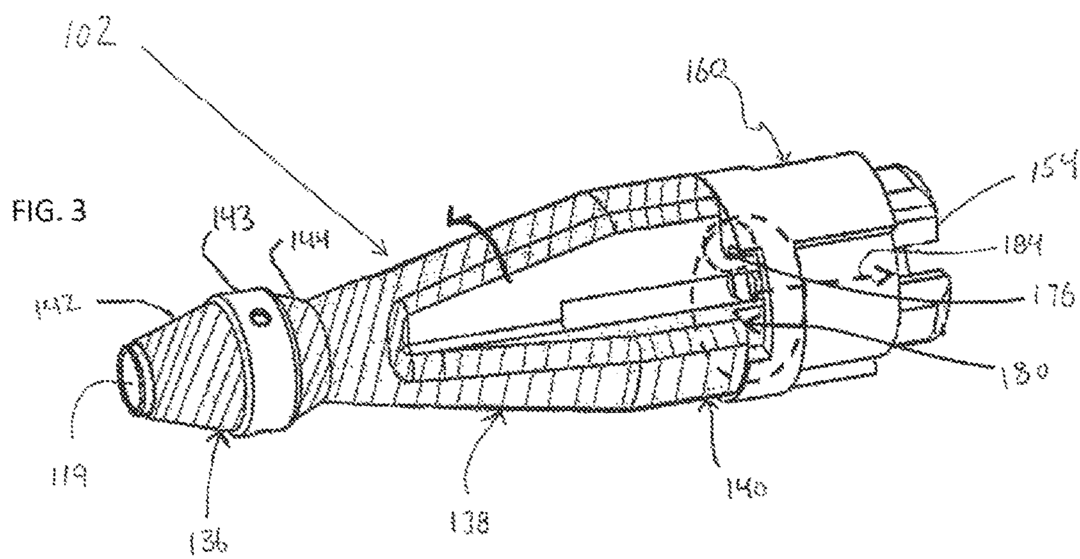
FIG. 3 is a perspective view of one version of the treatment member forming part of the medical device shown in FIG. 1.
Figure 4:
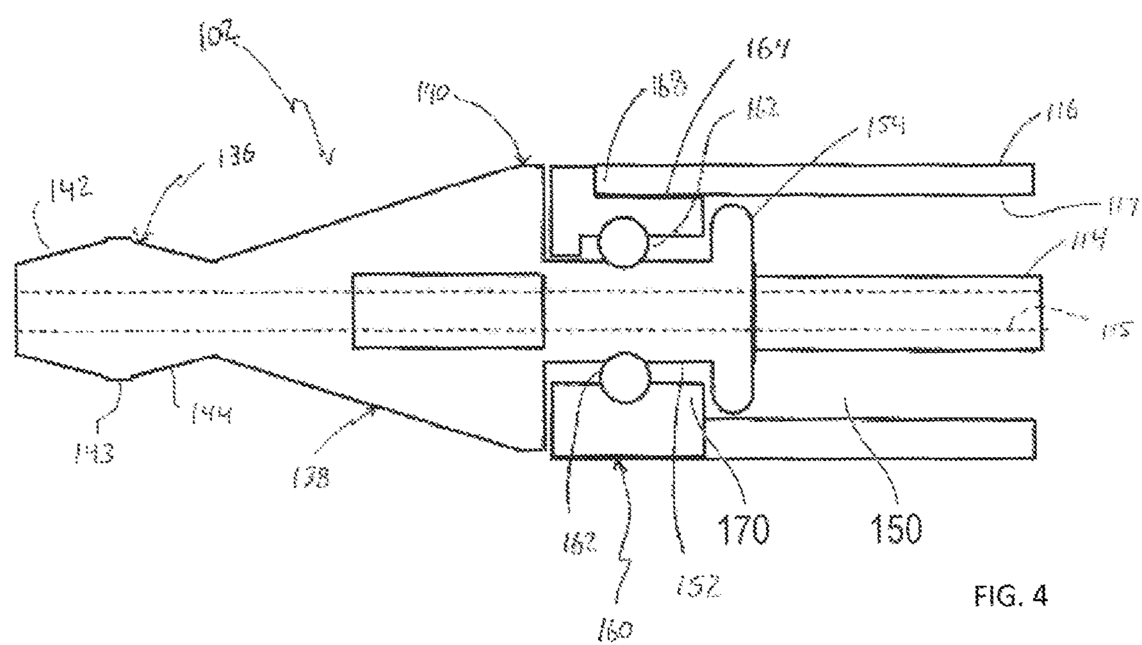
FIG. 4 is a cross-sectional view of the treatment member illustrated in FIG. 3.

FIGS. 3 and 4 illustrate additional details associated with the treatment member 102 that is connected to the distal end of the drive shaft 114. FIGS. 3 and 4 illustrate the centrally located guidewire lumen 115 that may be centrally provided in the drive shaft 114 for receiving a guidewire as discussed above. As mentioned above, during operation of the medical device, the distal end portion of the treatment member 102 is positioned distally beyond the distal-most end of the outer sheath 116. FIGS. 3 and 4 show that the treatment member 102 that extends distally beyond the distal-most end of the tubular outer sheath 116 and is thus exposed (for example, the treatment member 102 not covered by the outer sheath 116). The treatment member 102 that is exposed distally beyond the distal end of the outer sheath 116 during operation may be comprised of a distal-most end portion 136, an intermediate portion 138 and a proximal end portion 140. The intermediate portion 138 is positioned axially between the distal-most end portion 136 and the proximal end portion 140. The distal-most end portion 136, the intermediate portion 138 and the proximal end portion 140 may preferably be configured to facilitate grinding of the substance in the body lumen (e.g., stenosis S in a blood vessel BV). One way of accomplishing this result is to provide the distal-most end portion 136, the intermediate portion 138 and the proximal end portion 140 of the treatment member 102 with a coating that helps facilitate the grinding of the substance in the body lumen. An example of the coating is a diamond grind coating.

The distal-most end portion 136 of the treatment member 102 is comprised of a distally tapering portion 142 and a proximally tapering portion 144. The proximally tapering portion 144 is positioned proximal of the distally tapering portion 142. The distally tapering portion 142 constantly tapers in a narrowing manner towards the distal-most end of the treatment member 102 while the proximally tapering portion 144 constantly tapers in a narrowing manner towards the proximal-most end of the treatment member 102. The distal-most end portion 136 of the treatment member 102 also comprises a constant outer diameter intermediate portion 143 positioned between the distally tapering portion 142 and the proximally tapering portion 144. In the illustrated embodiment, the coating that helps facilitate the grinding of the substance in the body lumen is not provided on the constant outer diameter intermediate portion 143. Of course, the coating applied to the outer surface of the remainder of the treatment member 102 may also be provided on the outer surface of the constant outer diameter intermediate portion 143.

The intermediate portion 138 may be a tapering portion as illustrated in FIGS. 3 and 4 in which the intermediate portion tapers in a constant manner along its entire extent from the proximal-most end of the intermediate portion 138 to the distal-most end of the intermediate portion 138. The intermediate portion 138 tapers towards the distal-most end of the treatment member 102 so that the outer diameter of the intermediate portion 138 gradually narrows in the distal direction. The proximal end portion 140 may possess a constant outer diameter along its entire axial extent as shown in FIGS. 3 and 4.

The treatment member 102 is also provided with at least one window or through opening 150 that communicates with the hollow interior or lumen inside the treatment member 102. The treatment member 102 may include a plurality of circumferentially spaced-apart windows or through openings 150. As mentioned above, each of the windows or through openings 150 opens into and communicates with the hollow interior or lumen (gateway lumen) in the treatment member 102. The lumen or hollow interior of the treatment member 102 is in communication with the lumen 117 in the outer sheath 116 as shown in FIG. 4. The aspiration tube 112 shown in FIG. 1 is connected to or fluidly communicates with the lumen 117 in the outer sheath 116. The aspiration tube 112 is connected to an aspiration source or suction device 111 schematically illustrated in FIG. 1.

During operation of the medical device 100, the treatment member 102 is rotated by operation of the motor 128 to grind the substance 30 in the body lumen 10 (e.g., stenosis in the blood vessel). While the treatment member 102 is grinding the substance in the body lumen, the suction source 111 is operated to draw debris resulting from the grinding operation through the windows or through openings 150 in the treatment member 102, into the lumen or hollow interior in the treatment member 102, and into the lumen 117 in the outer sheath 116. The debris is then drawn out of or removed from the body lumen by way of the suction device 111.

As illustrated in FIG. 4, the proximal end portion of the treatment member 102 includes a reduced outer diameter portion defining a shaft portion 152 of the treatment member 102. This reduced-outer diameter shaft portion 152 of the treatment member 102 represents a seating region for receiving an outer tubular member 160 representing a shaft bearing or bush member. A lumen extends throughout the entire axial extent of the outer tubular member 160 (i.e., passes through the outer tubular member 160), and the reduced-outer diameter shaft portion 152 of the treatment member is positioned in the lumen that extends throughout the entire axial extent of the outer tubular member 160. The tubular member 160 is rotatable relative to the treatment member 102. That is, as described above, the treatment member 102 is rotatably driven by way of the drive shaft 114, and the treatment member 102 rotates relative to the tubular member 160.

An axially extending lumen extends throughout the entire length of the reduced-outer diameter shaft portion 152 (for example, passes through the reduced-outer diameter shaft portion 152). This lumen in the reduced-outer diameter shaft portion 152 communicates with and is coaxial with the lumen 115 in the drive shaft 114. The lumen in the reduced-outer diameter shaft portion 152 is also coaxial with the open end 119 at the distal-most end of the treatment member 102 shown in FIG. 3 and opens into and communicates with the lumen in the treatment member 102.

A bearing may be positioned between the outer surface of the reduced outer diameter shaft portion 152 and the inner surface of the outer tubular member 160 to facilitate the relative rotation between the reduced outer diameter shaft portion 152 and the outer tubular member 160. The bearing may be of any desired configuration, including a plurality of roller bearings 162 as shown in FIG. 4. The roller bearings 162 help facilitate relative rotation between the treatment member 102 and the outer tubular member 160.

As illustrated in FIG. 4, the outer peripheral surface of the outer tubular member 160 may be recessed to define a radially inwardly recessed portion defining a recess 164. The recess 164 is of limited circumferential extent (i.e., the recess 164 does not extend around the entire circumferential extent of the outer tubular member 160) so that the recess 164 possesses a circumferential extent less than 360°, preferably less than 180°. The recess 164 extends from the proximal-most end of the outer tubular member 160 towards the distal end of the outer tubular member 160. The recess 164 thus opens to the proximal-most end of the outer tubular member 160 and extends less than the entire axial extend of the outer tubular member 160 so that the distal-most end of the recess 164 is defined by a wall 166. FIG. 4 illustrates that the recess 164 in the outer surface of the outer tubular member 160 receives a distally extending projection at the distal end portion of the outer sheath 116. The engagement between the distally extending projection 168 of the outer sheath 116 and the recess 166 in the outer tubular member 160 rotationally fixes the outer sheath 116 and the outer tubular member 160 so that the outer sheath 116 and the outer tubular member 160 do not rotate relative to each other. Thus, when the treatment member 102 is rotated by operation of the motor 128, the treatment member 102 rotates relative to both the outer sheath 116 and the outer tubular member 160. The outer tubular member 160 may also include at least one radially inwardly directed protrusion 170.

Figure 5A:
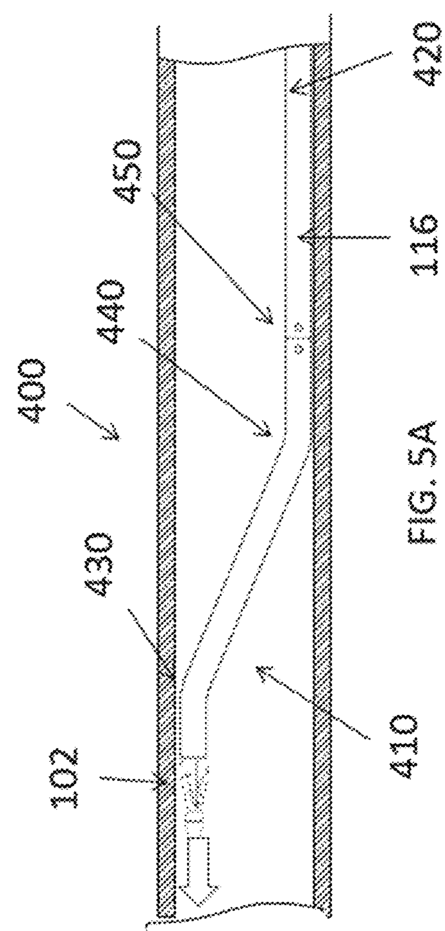
FIG. 5A is an illustration of a medical device having an outer tubular member in accordance with an exemplary embodiment.

FIG. 5A is an illustration of a medical device 100 having an outer tubular member 400 in accordance with an exemplary embodiment. As shown in FIG. 5A, the outer tubular member 400 includes a first tubular member 410 and a second tubular member 420. A connection 450 connects the first tubular member 410 to the second tubular member 420. In accordance with an exemplary embodiment, the outer tubular member 400, which is adjacent to the treatment member 102 includes a first bend (or first bend element) 430 and a second bend (or second bend element) 440. In accordance with an exemplary embodiment, the outer tubular member 400 is configured to be placed around the drive shaft 114 and inside the outer sheath 116, and is arranged on the distal end of the drive shaft 114 and the outer sheath 116 adjacent to the treatment member 102 (not shown in FIG. 5A or 5B).

Figure 5B:
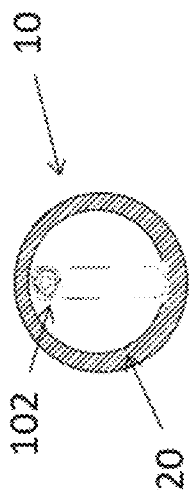
FIG. 5B is an end view of the medical device having the outer tubular member as shown in FIG. 5A in accordance with an exemplary embodiment.

FIG. 5B is an end view of the medical device 10 having the outer tubular member pre-bending portion 400 as shown in FIG. 5A in accordance with an exemplary embodiment. As shown in FIG. 5B, the second tubular member 420 preferably in contact with the vessel wall 20 on one side and the first tubular member 410 is in contact with the vessel wall 20 on an opposite side, for example, 180 degrees to one another.

Figure 6:
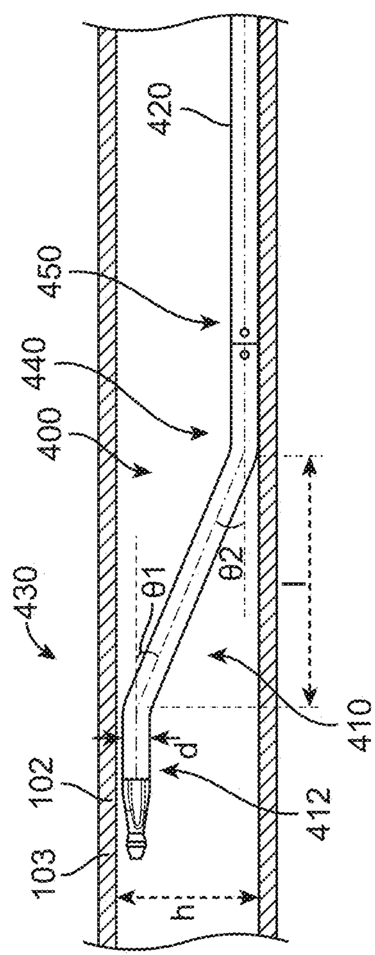
FIG. 6 is an illustration of a medical device having an outer tubular member in accordance with an exemplary embodiment.

FIG. 6 is an illustration of a medical device 100 having an outer tubular member 400 in accordance with an exemplary embodiment. As shown in FIG. 6, in a natural state (for example, a packaged state), the outer tubular member 400 of the device 100 has a least one first bend element 430 including a distal end portion of the outer tubular element and a second bend element 440 proximal to the first bend element 430. Advantageously, the at least the first bend element 430 and the second bend element 440 can contact a vessel wall at the same time. The first bend element 430 is configured to redirect a tip 103 of treatment member 102 in order not to face the tip 103 toward a vessel wall 20 during use for safety. In addition, the second bend element 440 is configured to enhance a contact force against the vessel wall 20.

In accordance with an exemplary embodiment, an outer diameter of the outer tubular member 400 is preferably less than or equal to an outer diameter of the treatment member 102. In accordance with an exemplary embodiment, there is a possibility that it cannot penetrate the vessel wall, if the outer diameter of the outer tubular member 400 is larger than that of the treatment member 102.

As shown in FIG. 6, the first bend element 430 and the treatment member 102 are substantially coplanar in state of contact with the vessel wall 20, which helps the treatment member 102 to safely contact the vessel wall 20. In accordance with an exemplary embodiment, the outer diameter of the treatment member 102 is larger than the outer diameter of the outer tubular member 400. In accordance with an exemplary embodiment, the difference between the outer diameters of the treatment member 102 and the outer tubular member 400 is smaller than the blood vessel wall 20. This helps prevent perforation of the vessel wall 20 if the treatment member 102 is inserted into a vessel lumen which has a smaller inner diameter than the outer diameter of the treatment member 102. In accordance with an exemplary embodiment, the treatment member can be rotated while the treatment member is positioned adjacent to the substance to be ground in the living body and grinding the substance without withdrawing a coated wire or coated guidewire. In accordance with exemplary embodiment, for example, the coated wire or coated guidewire has a coating, which is hydrophobic to improve the capacity of the sliding of the coated wire or guidewire in the vessel.

In accordance with an exemplary embodiment, in the natural state (packaged state), as shown in FIG. 6, d is an outer diameter of first tubular member 410, h is an inner diameter of a target blood vessel lumen, θ1 is an angle (R1) in degrees of the first bend element 430, θ2 is an angle (R2) in degrees of the second bend element 440, and l is a length between the first bend element 430 and the second bend element 440. In accordance with an exemplary embodiment, R1 is preferably equal to R2. For example, in case of R1=R2 (R1 equal to R2), it would be able to work in a vessel 10 that has the inner diameter <h (less than h). In case of R1>R2 (R1 greater than R2), it would be able to work in a vessel 10 that has the inner diameter>h (greater than h), and in case of R1<R2 (R1 less than R2), the tip 103 of the treatment member 102 faces toward the inside of a vessel 10, which is relatively safe.

In accordance with an exemplary embodiment, the outer tubular member 400 is preferably composed of one or more rigid materials. For example, the one or more rigid materials can be one or more materials, which can maintain a natural state, and be difficult to change a straight line, and wherein the natural state is a state in which, for example, the outer tubular member 400 in not limited (or constrained) by something, for example, a vessel wall. In accordance with an exemplary embodiment, for example, as shown in FIG. 6, the outer tubular member 400 is comprised of the first tubular member 410, which is preferably Nitinol, and the second tubular member 420 is preferably, for example, stainless steel (SUS), and the connecting part (or connector) 450. In accordance with an exemplary embodiment, by using a shape memory alloy as the material of the bend member, it is possible to obtain a predetermined shape, elastic force (contact force) against a blood vessel by its characteristic. In case of stainless steel (SUS), the shape can be changed from the original shape during the procedure.

In accordance with an exemplary embodiment, rigidity of a distal end 412 of the first tubular member 410 is higher than one of the first bend element 430. Since the distal end of the treatment member is linearly aligned with the first tubular member 410, the surface of the treatment member is likely to contact a blood vessel wall or the lesion. As shown in FIG. 6, the first bend element 430 and the second bend element 440 are located in the first tubular member 410. In accordance with an exemplary embodiment, the connection part (or connector) 450 is located on the straight part of the outer tubular member 400, which can efficiently transmit the pushability transmitted by the second tubular member 420 to the first tubular member 410.

In accordance with an exemplary embodiment, the first bend element 430, the second bend element 440, and the treatment member 102 helically contact in a blood vessel wall 20. For example, when a proximal end of the first tubular member 410 is pushed, the treatment member 102 can advance helically and can remove vascular occlusion material in the circumferential direction. In addition, the outer tubular member 400 can rotate while maintaining the state in which a guide wire does not rotate with the first bend element 430, while the first bend element 430 and treatment member 102 in state of contact with a vessel wall 20, which helps prevent damage to a guide wire FIG. 7A is an illustration of a first tubular member 410 of the outer tubular member 400 in accordance with an exemplary embodiment. As shown in FIG. 7A, the first tubular member 410 is preferably a shaped memory alloy, for example, a Nitinol tube with laser cutting.

Figure 7B:
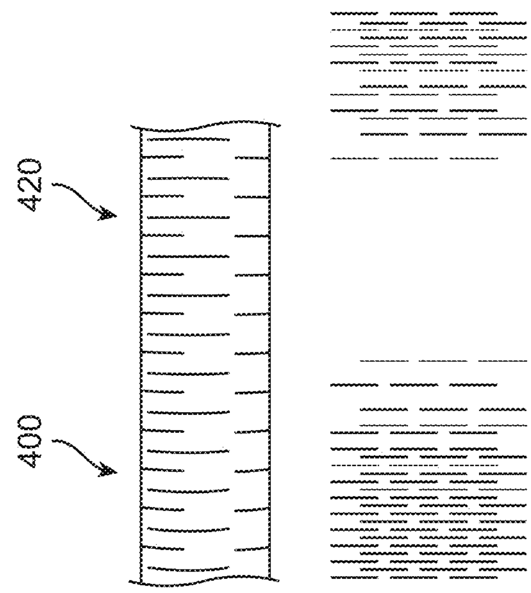
FIG. 7B is an illustration of a second tubular member of the outer tubular member in accordance with an exemplary embodiment.
Figure 7A:
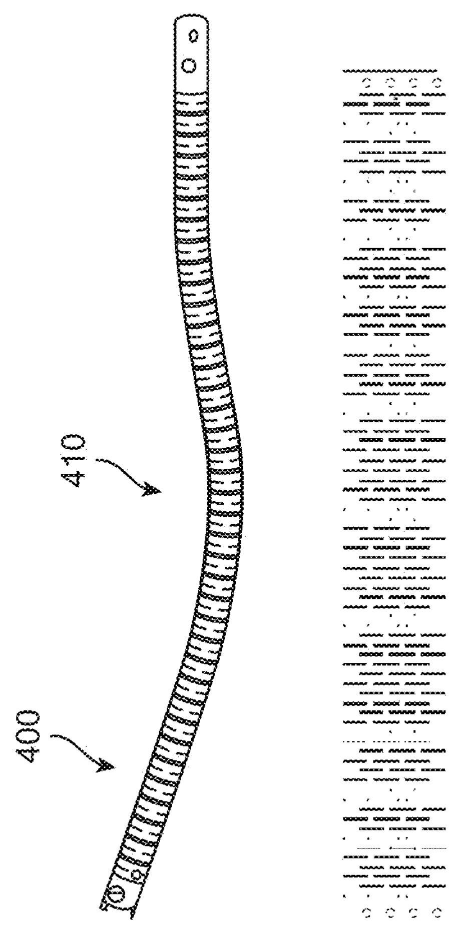
FIG. 7A is an illustration of a first tubular member of the outer tubular member in accordance with an exemplary embodiment.

FIG. 7B is an illustration of a second tubular member 420 of the outer tubular member 400 in accordance with an exemplary embodiment. As shown in FIG. 7B, the second tubular member 420 is configured to transmit torque to the first tubular member 410 and the treatment member 102 and is preferably a stainless tube with laser cutting or a braided tube.

Figure 8A:
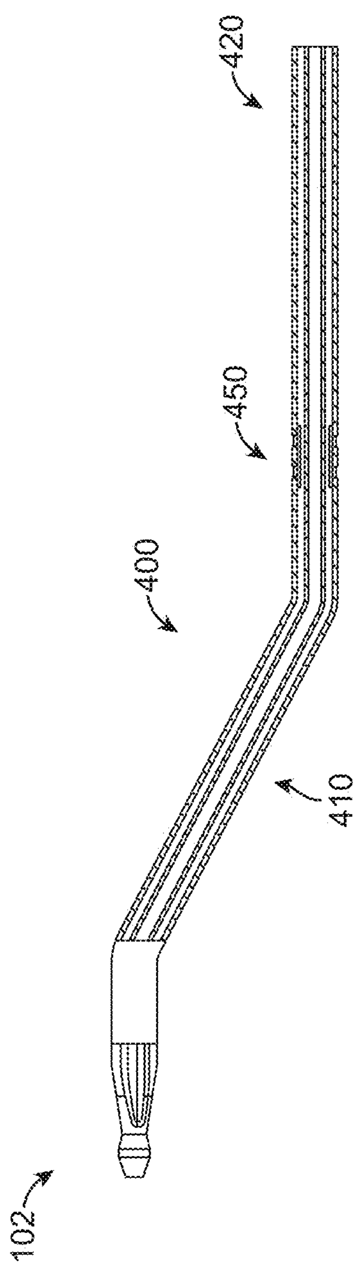
FIG. 8A is an illustration of the medical device having an outer tubular member in accordance with an exemplary embodiment.
Figure 8B:
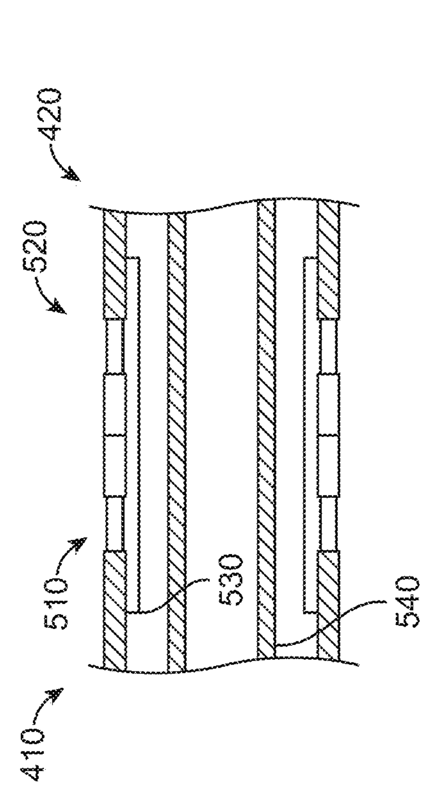
FIG. 8B is a cross-sectional view of the connection portion as shown in FIG. 8A in accordance with an exemplary embodiment.

FIG. 8A is an illustration of the medical device 100 having an outer tubular member 400 and the connection portion 450 in accordance with an exemplary embodiment. FIG. 8B is a cross-sectional view of the connection portion 450 as shown in FIG. 8A in accordance with an exemplary embodiment. As shown in FIG. 8B, the connection portion 450 includes a plurality of holes 510 on the first tubular member 410 and a plurality of holes 520 on the second tubular member 420 and a joint member 530, which solder is placed into the plurality of holes 510, 520 to connect the first tubular member 410 to the second tubular member 420. In accordance with an exemplary embodiment, the joint member 530 is a stainless steel tube. As shown, the plurality of holes 510, 520 extend through an outer circumference of each of the first and the second tubular members 410, 420. The number of holes 510, 520 is at least two (2) and can be, for example, two (2) to eight (8), and more preferably two (2) to four (4) holes.

Figure 9B:
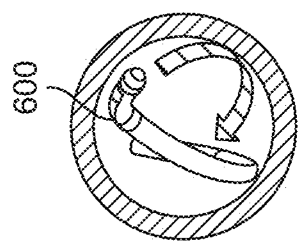
FIG. 9B is an end view of the helical outer tubular member as shown in FIG. 9A in accordance with an exemplary embodiment.
Figure 9A:
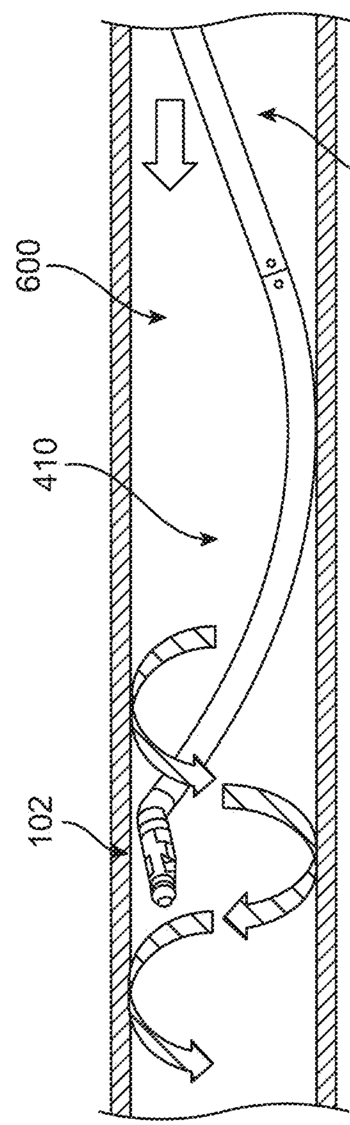
FIG. 9A is an illustration of another exemplary embodiment of a medical device having a helical outer tubular member in accordance with an exemplary embodiment.

FIG. 9A is an illustration of another exemplary embodiment of a medical device 100 having an outer tubular member 400. FIG. 9B is an end view of the medical device 100 having a pre-bending portion of the outer tubular member 400 as shown in FIG. 9A in accordance with an exemplary embodiment. As shown in FIGS. 9A and 9B, the first and the second tubular elements 410, 420, can be configured to have a helical (or spiral) configuration 600.

Figure 10:
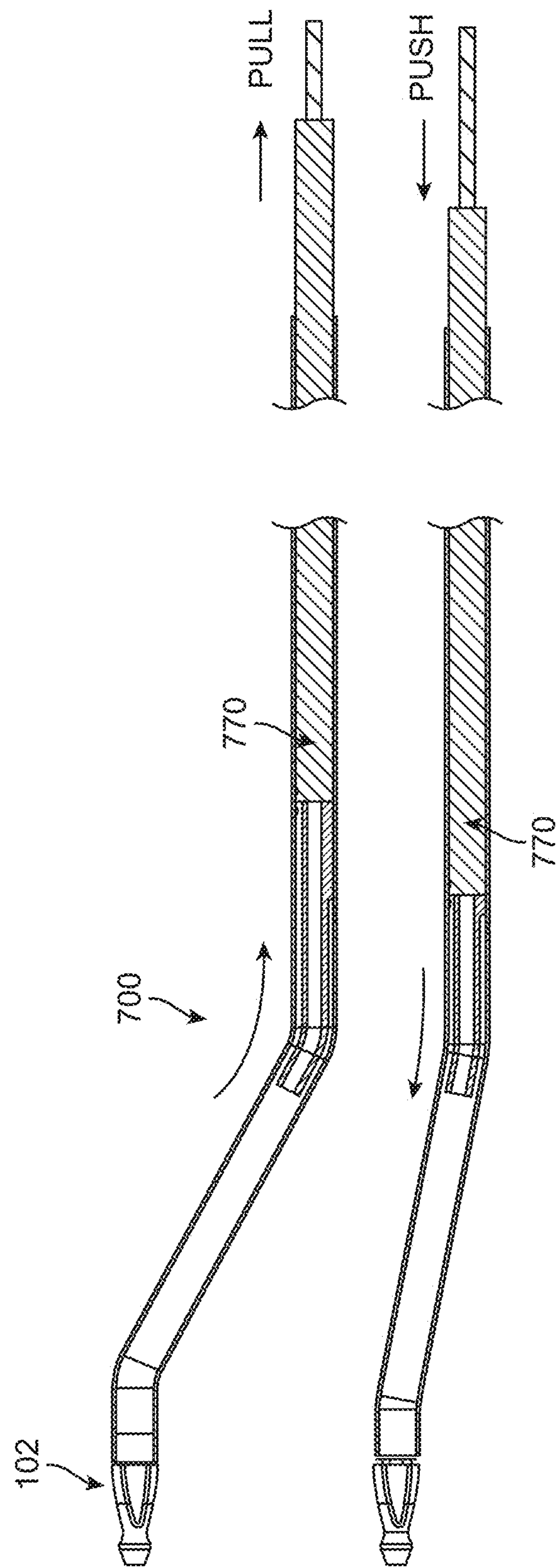
FIG. 10 is an illustration of a medical device having a manual bending portion in accordance with another exemplary embodiment.

FIG. 10 is an illustration of a medical device 100 having a manual bending member 700 in accordance with another exemplary embodiment. As shown in FIG. 10, the manual bending member 700 can be bent by pushing or pulling an operation member 770. For example, as shown in FIG. 10, upon pulling of the operation member 770 proximally, for example towards the handle, the curvature of the manual bending member increases. Meanwhile, upon pushing the operation member distally, the curvature of the manual member decreases (i.e., becomes relatively flat or straight).

In accordance with an exemplary embodiment, a method is disclosed, which includes introducing a treatment member on a distal end portion of an inner member, the inner member comprises a bendable part and a transmission part, an operation member; and an outer tubular member, wherein the bendable part is fixed to both the outer tubular member and the operation member, and the operation member is configured to move axially relative to the outer tubular member. The inner member and the outer tubular member can be bent to one direction while moving the operation member of the inner tubular member to the axial direction. The treatment member is rotated in the bending state while the treatment member is positioned adjacent to the substance to be ground in the living body to grind the substance, and shearing debris resulting from the grinding of the substance to reduce a size of the debris. In accordance with an exemplary embodiment, a second bending the inner member and the outer tubular member to other directions while moving the operation member of the inner tubular member to an opposite axial direction.

Figure 11A:
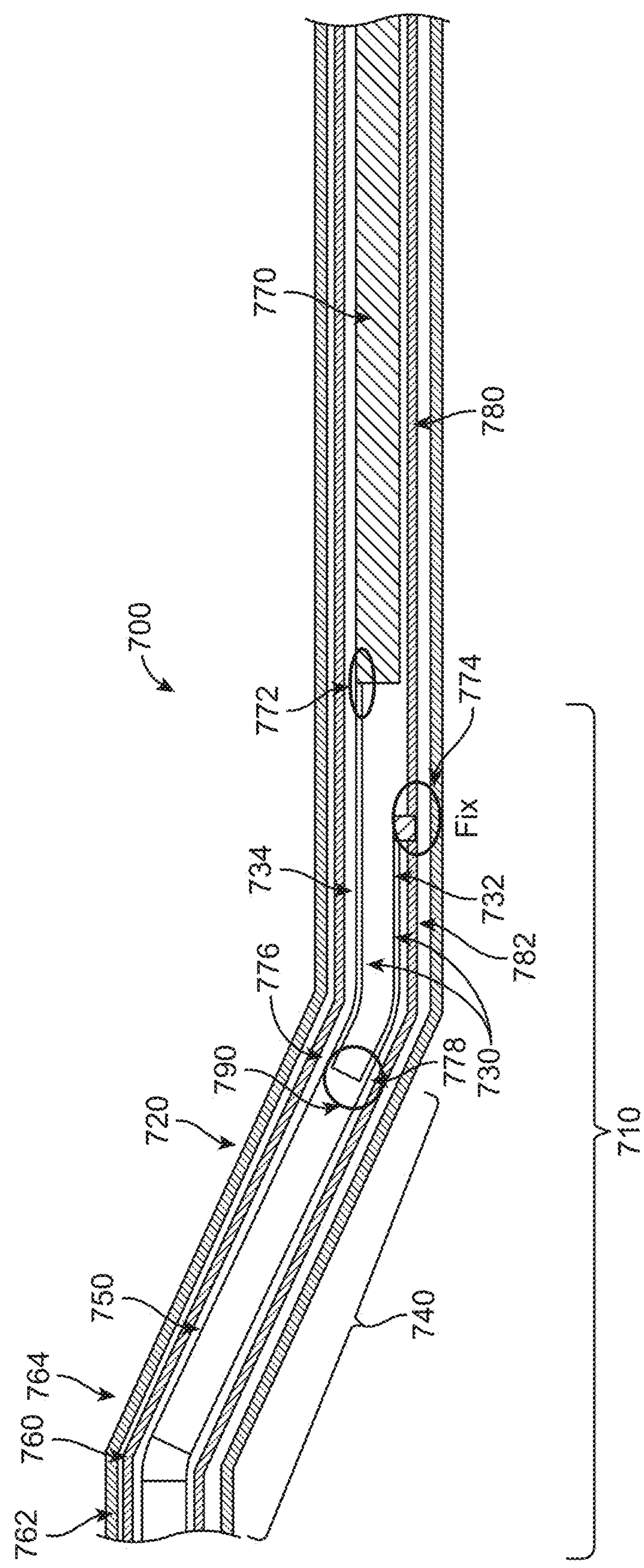
FIG. 11A is an illustration of a medical device having a manual bending portion in accordance with another exemplary embodiment.

FIG. 11A is an illustration of a medical device 100 having a manual bending member 700 in accordance with another exemplary embodiment. As shown in FIG. 11, the manual bending member 700 can be arranged within an outer housing (or outer layer) 720 and can include an inner member 710 and an operation member 770. The inner member 710 comprises at least a bendable part 730 configured of a plural members 732, 734. The inner member 710 may have a transmission part 740. The transmission part 740 is preferably a tubular member (i.e., an inner tubular member) 750. In accordance with an exemplary embodiment, the bendable part 730 is fixed to a proximal end 776, 778 of the transmission part 740 and is fixed to a distal portion 774 of the outer tubular member 780 and a distal end 772 of the operation member 770. The operation member 770 is axially movable relative to the outer tubular member 780. In accordance with an exemplary embodiment, the transmission part 740 may be the same as the bendable part 730. For example, the transmission part 740 may be a rigid member that is more rigid than the bendable part of the inner member 710. In addition, the rigid member can rather easily transmit the force received from the operation member. In accordance with an exemplary embodiment, the rigid member of the inner member 710 is more rigid than the bendable part 730 of the inner member 710.

In accordance with an exemplary embodiment, the outer tubular member 780 in which the bendable part 730 of the inner member 710 is located is flexible. The outer tubular member 780 comprises at least two parts, a rigid member or rigid part of the outer tubular member 780, and a flexible member 782 of the outer tubular member 780. The flexible member 782 of the outer tubular member 780 is located in an outwardly radial direction of the bendable part 730 of the inner member 710. The outer tubular member 780 may comprise only flexible part that can bend with the bendable part 730 of the inner member 710. The flexible member 782 is more flexible than the transmission part 740 that can bend.

In accordance with an exemplary embodiment, the bendable parts 730 are each disposed at 180 degrees to one another. For example, the bendable part 730 can be arranged in diagonal positions to one another in the circumferential direction and axially movable relative to one another. In addition, the transmission part 740 of the inner member 710 can be fixed to the bendable part 730 of the inner member 710 by a joint part (or connection joint) 790, which can help preset an optimal contact force in the blood vessel for example, for safety. The transmission part 740 may be a flat member or a tubular member.

In accordance with an exemplary embodiment, the transmission part 740 of the inner member 710 can have a pre-shaped part (or member) 760, which can also help preset an optimal contact force in the blood vessel for safety. For example, the pre-shaped part (or member) 760 can have a defined curvature or an angle between a distal side 762 and a proximal side 764. In accordance with an exemplary embodiment, a portion of the outer tubular member 780 in which the transmission part 740 of the inner member 710 can be flexible.

Figure 11B:
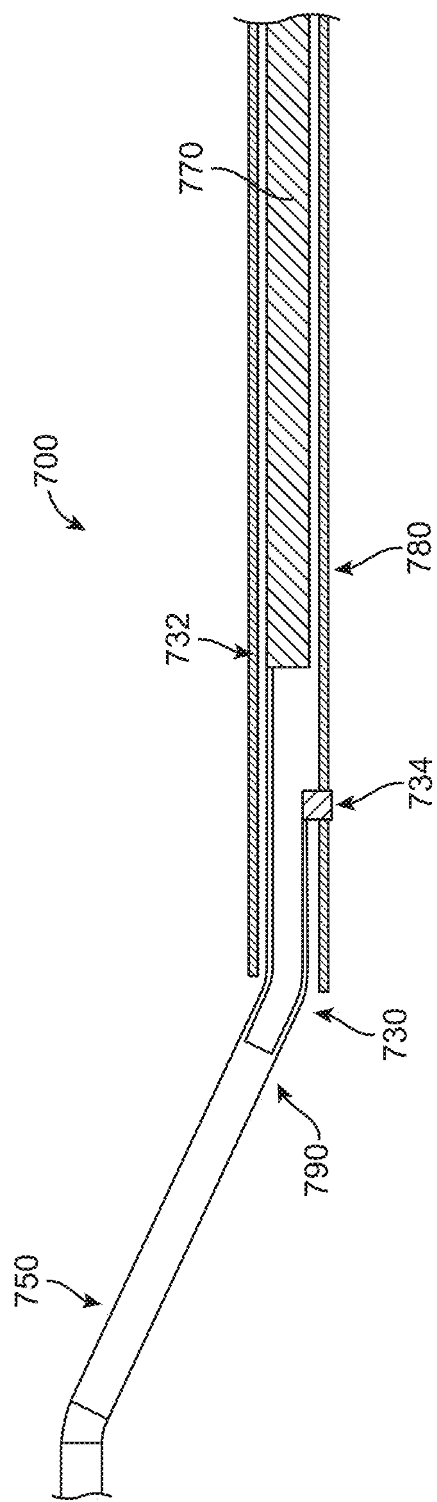
FIG. 11B is an illustration of a medical device having a manual bending member in accordance with another exemplary embodiment.

In accordance with an exemplary embodiment as shown in FIG. 11B, the outer tubular member 780 can terminate proximally of the joint part (connection joint) 790. Thus, an outer diameter of the distal side of the medical device 100 can be relatively smaller than with the outer tubular member 780 extending to the treatment member 102.

In accordance with an exemplary embodiment, the bendable part 730 can be adapted to preferentially bend in one direction, which can help reduce the required tensile force required for bending. The operation member 770 can be a tubular member, which can help resolve the issues, for example, wherein a wire is pulled, and wherein the bending of the outer tubular member 780 affects the bending to the bendable part 730. In accordance with an exemplary embodiment, the length of each of the bendable members 732, 734 is different such that the manually bending member 700 can be bent bi-directionally. In accordance with an exemplary embodiment, a long bendable member of the at least two bendable members having different lengths is fixed to the outer tubular member and a short bendable member of the at least two bendable members is fixed to the operation member. In accordance with an alternative embodiment, the operation member 770 can be a wire.

In accordance with an exemplary embodiment, the transmission part 740 of the inner member 710 is a tubular member or a flat member. As shown, the bendable part 730 of the inner member 710 is a plural number. In accordance with an exemplary embodiment, the material of the inner tubular member 750 is different from the material of the operation member 770. For example, it is possible to set different rigidity, elasticity only at the inner tubular member 750, for example, for enhancing contact force against a vessel wall 20.

Figure 11C:
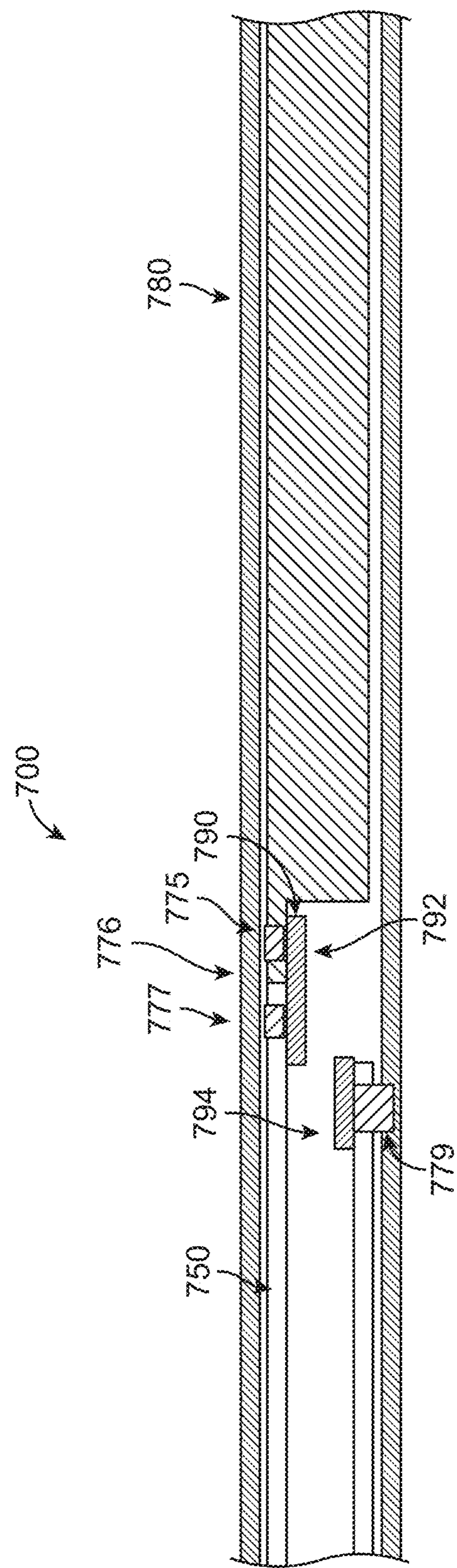
FIG. 11C is an illustration of a medical device having a manual bending member in accordance with another exemplary embodiment.

FIG. 11C is an illustration of a medical device having a manual bending member 700 in accordance with another exemplary embodiment. As shown in FIG. 11C, in accordance with an exemplary embodiment, the manual bending member 700 has a joint member 790 configured to connect the inner tubular member 750 and the operation member 770. The position of the distal end face 776 of the operation member 770 is different in the axial direction for connecting the inner tubular member to the operation member than a non-connecting distal end face of the operation member. The difference of the distal end face 776 of the operation member which can help maintain the inner lumen. In accordance with an exemplary embodiment, as shown in FIG. 11C, the inner tubular member 750 can be soldered though at least one hole 775, 777 in the inner tubular member 750 and the operation member 770, for example, to a plate 792, which joins the distal end 776 of the operation member 780. In addition, the inner tubular member 750 can be soldered through at least one hole 779 to a second plate 794, which joins a proximal end of the inner tubular member 750 to the outer tubular member 780.

In accordance with an exemplary embodiment, an outer layer 720 on an outer surface of the outer tubular member 780 can be used to help seal for suction or flushing of fluid and/or debris during use. In addition, an inner layer (not shown) on the surface of the inner tubular member 750 can be used to seal for suction or flushing of fluid and/or debris during use. In accordance with an exemplary embodiment, the outer layer 720 and/or inner layer of the inner tubular member 750 can be, for example, PTFE polymer or a shrink-wrap material, which seals an outer surface and/or an inner surface of the inner tubular member 750

Figures 12A, 12B, 12C:
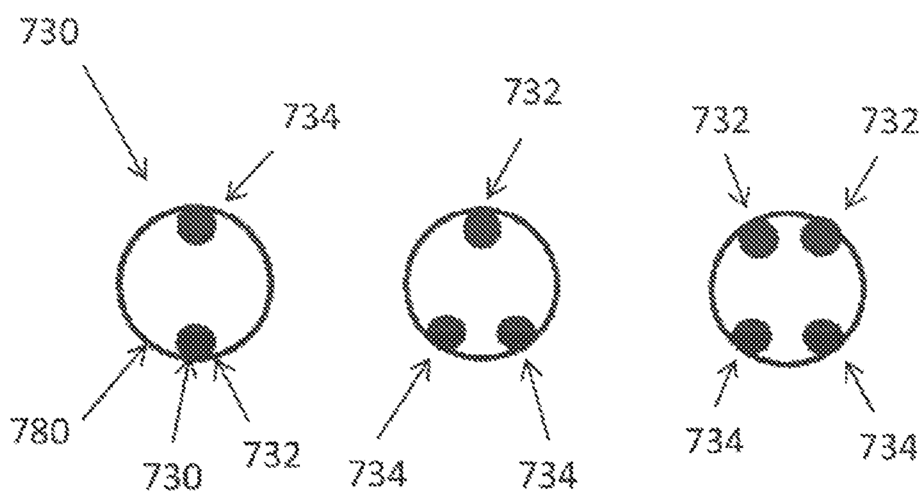
FIGS. 12A-12C are illustrations of a plurality of vertical section views of the manual bending member in accordance with an exemplary embodiment.

FIGS. 12A-12C are illustrations of a plurality of vertical section views of the manual bending member 700 in accordance with an exemplary embodiment. As shown in FIGS. 12A-12C, the bendable part 730 of the inner member 710 is a plural number.

For example, as shown in FIG. 12A, the outer tubular member 780 in which the bendable part 730 of the inner member 710 is located is flexible, and the bendable parts 730 are each disposed at 180 degrees to one another. For example, the bendable members 732, 734 can be arranged in diagonal positions to one another in the circumferential direction. In addition, the bendable member 732, 734 are configured to be axially movable relative to one another.

As shown in FIG. 12B, the bendable parts can be arranged to have one bendable member 732 fixed to the operation member 770 and two bendable members 734 fixed to the outer tubular member 780. For example, as shown in FIG. 12B, the bendable members 732, 734 can be arranged at an equal positions to one another in the circumferential direction from each other, for example, at 120 degrees, or alternatively, the two bendable members 734 can be arranged at an equal circumferential position from an opposing bendable member 732 arranged at 180 degrees to a center point between the two bendable members 734.

In FIG. 12C, the bendable part 730 can include at least two bendable members 732 connected to the operation member 780 and at least two bendable members 734 connected to the outer member 780. As shown in FIG. 12C, the bendable parts 732, 734 are preferably arranged at equal positions in the circumferential direction and are axially movable relative to one another.

FIG. 13A is an illustration of a portion of a medical device 100 having a manual bending member 700 in accordance with another exemplary embodiment. As shown in FIG. 13A, the first inner tubular member 750 can be a shape memory allow, for example, Nitinol with laser cutting. In accordance with an exemplary embodiment, the first inner tubular member 750 has a relatively flat cross-sectional shape.

FIG. 13B is an illustration of a portion of a medical device 100 having a manual bending member 700 in accordance with another exemplary embodiment. As shown in FIG. 13B, the operation member 770 can be a tubular member 772 having a low elongation rate and is flexible. For example, in accordance with an exemplary embodiment, the operation member 770 is a stainless steel tube with laser cutting or a braided tube.

FIG. 13C is an illustration of a portion of a medical device 100 having a manual bending member 700 in accordance with another exemplary embodiment. As shown in FIG. 13C, the outer tubular member 780 preferably has high torque response with a low elongation rate, a low compression rate, and is flexible on the bendable part 730. For example, in accordance with an exemplary embodiment, the outer tubular member 780 is a stainless steel tube with laser cutting or a braided tube.

Figure 14:
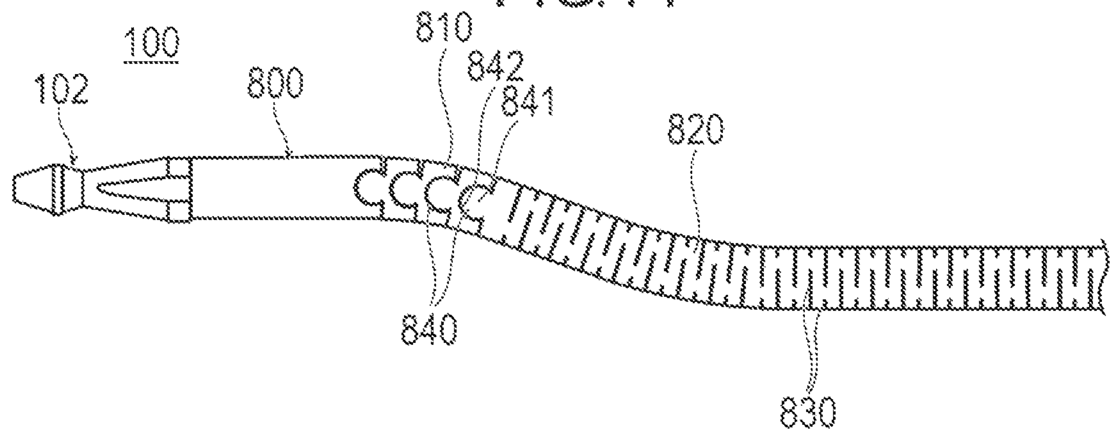
FIG. 14 is an illustration of a portion of a medical device having a manual bending member in accordance with another exemplary embodiment.
Figure 15:
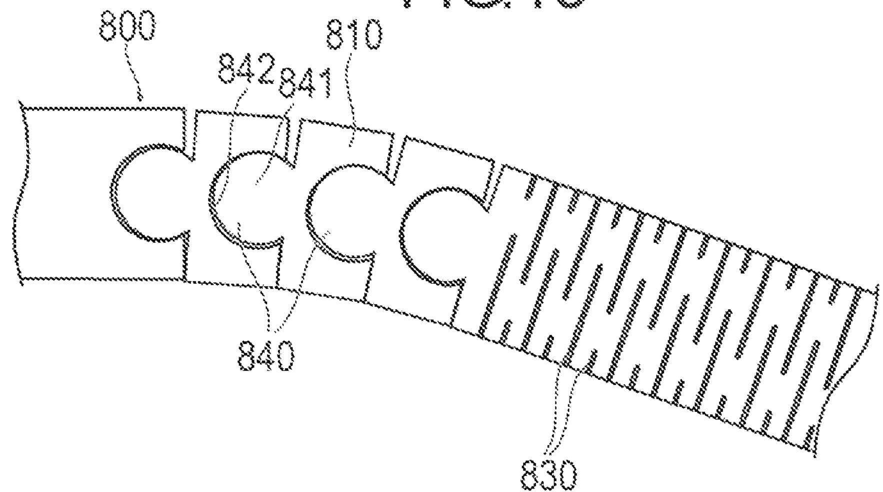
FIG. 15 is an illustration of a first tubular member of the outer tubular member in accordance with an exemplary embodiment.

FIGS. 14 and 15 illustrate another embodiment of a medical device 100. In accordance with an exemplary embodiment, an outer tubular member 800 of the medical device 100 is provided with a first bend element 810 and a second bend element 820. The second bend element 820 is located at a distal side of the first bend element 810 and bent to a direction substantially opposite to the first bend element 810. Portion of the outer tubular member 800 which is located at a proximal side than the first bend element 810 is formed with a plurality of slits 830 extending to a circumferential direction. The plurality of slits 830 are formed, for example, by laser cutting. Each of the slits 830 is perpendicular to a shaft center of the outer tubular member 800, but it may not necessary be perpendicular. The slits 830 are formed with a length less than 360 degrees to the circumferential direction of the outer tubular member 800. Accordingly, the outer tubular member 800 has a portion which is not cut by the slits 830 per circumference. Thus, torque transmission efficiency of the outer tubular member 800 is enhanced, which in turn facilitates to change direction of a tip of the outer tubular member 800 to the circumferential direction by operating the proximal portion of the outer tube member 800. Further, push-in force against a stenosis of the treatment member 102 is enhanced, by providing the first bend element 810 and the second bend element 820. Thus, grinding force of the treatment member is improved. The first bend element 810 of the outer tubular member is formed with at least one joint 840 aligned in an axial direction. The joint 840 has a concave part 841 and a convex part 842 fitted with each other in a relatively rotatable manner. The concave part 841 and the convex part 842 can be formed to be cut apart, for example, by laser cutting. The convex part 842 is partially circular. The concave part 841 is formed in an ark shape to rotatably surround the circular portion of the concave part 841. The convex part 842 can be rotated inside the concave part 841 within the prescribed range, but do not separate from the concave part 841. Further, the form of the joint 840 is not particularly limited. The joint 840 can thus have a form that is easier to bend only to one side. Thus, the outer tubular member 800 exhibits high trackability at the distal portion which is rather easily bent. When the guide wire is inserted in the joint 840, the joint 840 can be moved along the form of the guide wire.

It should be noted that the present invention is not limited only to the above-described embodiments, and the technical ideas of the present invention. Various modifications are possible by those skilled in the art. In addition, the living body lumen into which the medical device is inserted is not limited to a blood vessel, for example, it may be a vessel, ureter, bile duct, oviduct, hepatic duct and the like.

The detailed description above describes embodiments of a medical device and method for grinding substance from a body lumen representing examples of the inventive medical device and method disclosed here. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device, the medical device comprising:

an outer tubular member made from one or more rigid materials having a first bend element and a second bend element, the second bend element being proximal to the first bend element in a natural state;

a drive shaft and a rotatable treatment member configured to be accommodated in the outer tubular member, the treatment member on a distal end of the drive shaft, the treatment member configured to rotate and grind a substance inside a body lumen, the treatment member including a distal-most end portion, a proximal end portion, and an intermediate portion positioned axially between the distal-most end portion and the proximal end portion, and wherein the intermediate portion tapers toward the distal-most end portion of the treatment member from a proximal-most end of the intermediate portion to a distal-most end of the intermediate portion, and wherein the distal-most end portion, the proximal end portion, and the intermediate portion are configured to be exposed distally beyond a distal end of the outer tubular member and configured to grind the substance inside the body lumen, and at least a portion of the distal-most end portion and at least a portion of the intermediate portion includes a coating configured to help facilitate the grinding of the substance inside the body lumen; and the treatment member including at least one window that communicates with a lumen of the outer tubular member, and wherein the lumen of the outer tubular member is in communication with an aspiration tube configured to be connected to an aspiration source.

2. The medical device of claim 1, wherein the first bend element and the second bend element are configured to contact a vessel wall at a same time such that the first bend element is configured to redirect a tip of the treatment member in order not to face the tip toward the vessel wall and the second bend element is configured to enhance a contact force against the vessel wall on an opposite side of at least the first bend element.

3. The medical device of claim 1, wherein the first bend element and the treatment member are configured to be substantially coplanar in a state of contact with a blood vessel wall.

4. The medical device of claim 1, wherein in the natural state or a packaged state, and where d is an outer diameter of the outer tubular member, h is an inner diameter of a target blood vessel lumen, $\theta 1$ is an angle in degrees of the first bend element, $\theta 2$ is an angle in degrees of the second bend element, and l is a length between the first bend element and the second bend element, and wherein $\theta 1$ is equal to $\theta 2$.

5. The medical device of claim 1, wherein in the natural state or a packaged state, and where d is an outer diameter of the outer tubular member, h is an inner diameter of a target blood vessel lumen, $\theta 1$ is an angle in degrees of the first bend element, $\theta 2$ is an angle in degrees of the second bend element, and l is a length between the first bend element and the second bend element, in case of $\theta 1=\theta 2$, the medical device is configured to work in a vessel that has the an inner diameter less than h;

in case of $\theta 1>\theta 2$, the medical device is configured to work in the vessel that has the inner diameter greater than h; and in case of $\theta 1<\theta 2$, a tip of the treatment member is configured to face toward an inside the vessel.

6. The medical device of claim 1, wherein the outer tubular member is comprised a first tubular member and a second tubular member, the first tubular member being Nitinol and the second tubular member being stainless steel, and a connector between the first tubular member and the second tubular member.

7. The medical device of claim 6, wherein a rigidity of a distal end of the first tubular member is higher than a rigidity of the first bend element.

8. The medical device of claim 6, wherein the first bend element and the second bend element are located in the first tubular member.

9. The medical device of claim 6, wherein the connector is located on a straight part of the outer tubular member.

10. The medical device of claim 1, wherein the first bend element, the second bend element, and the treatment member are configured to helically contact a blood vessel wall.

11. The medical device of claim 1, wherein the outer tubular member is configured to rotate while maintaining a state in which a guide wire does not rotate with the first bend element, the second bend element, and the treatment member are in a state of contact with a vessel wall.

12. The medical device of claim 1, wherein the distal-most end portion of the treatment member includes a distal tapering portion, a proximal tapering portion, and a ring shaped portion between the distal tapering portion and the proximal tapering portion, the distal tapering portion and the proximal tapering portion including the coating configured to help facilitate the grinding of the substance inside the body lumen.

13. The medical device of claim 12, wherein the ring shaped portion has a constant outer diameter, and the coating on the distal tapering portion and the proximal tapering portion configured to help facilitate the grinding of the substance inside the body lumen is a diamond grind coating.

14. The medical device of claim 1, wherein the at least one window comprises a plurality of circumferentially spaced-apart windows.

15. The medical device of claim 1, further comprising: the aspiration source.

16. The medical device of claim 1, wherein the distal-most end portion of the treatment member includes a distal tapering portion and a ring shaped portion between the distal tapering portion and the intermediate portion; and a taper shape of the distal tapering portion is different from a taper shape of the intermediate portion.

17. A medical device, the medical device comprising:

an outer tubular member made from one or more rigid materials having a first bend element and a second bend element, the second bend element being proximal to the first bend element in a natural state;

a drive shaft and a rotatable treatment member configured to be accommodated in the outer tubular member;

the treatment member on a distal end of the drive shaft, the treatment member configured to rotate and grind a substance inside a body lumen by rotating about a central axis, the treatment member including a distal-most end portion, a proximal end portion, and an intermediate portion positioned axially between the distal-most end portion and the proximal end portion, the distal-most end portion, the proximal end portion, and the intermediate portion being configured to be exposed from a distal end of the outer tubular member and to grind the substance inside the body lumen, and wherein the distal-most end portion includes a distally tapering portion and a proximally tapering portion, the proximally tapering portion being proximal of the distally tapering portion, and an intermediate portion of the distal-most end portion located between the distally tapering portion and the proximally tapering portion of the distal-most end portion; and wherein a distal end surface of the treatment member is configured to be directed toward a central axis of a vessel.

18. The medical device of claim 17, wherein the first bend element is configured to redirect the distal end surface of the treatment member away from a wall of the vessel.

19. The medical device of claim 17, wherein a taper shape of the distally tapering portion of the distal-most end portion is different from a taper shape of the proximally tapering portion of the distal-most end portion.

20. A medical device, the medical device comprising:

an outer tubular member made from one or more rigid materials having a first bend element including a distal end portion of the outer tubular member and a second bend element, the second bend element being proximal to the first bend element in a natural state;

a drive shaft configured to be accommodated in the outer tubular member;

a rotatable treatment member on a distal end of the drive shaft, the treatment member configured to rotate and grind a substance inside a body lumen, the treatment member including a distal-most end portion, a proximal end portion, and an intermediate portion positioned axially between the distal-most end portion and the proximal end portion, and wherein the distal-most end portion includes a distally tapering portion and a proximally tapering portion proximal of the distally tapering portion, the distally tapering portion tapers toward a distal-most end of the treatment member, the proximally tapering portion tapers toward the proximal end portion, and the intermediate portion tapers toward the distal-most end of the treatment member from a proximal-most end of the intermediate portion to a distal-most end of the intermediate portion; and a bearing between the outer tubular member and the drive shaft, the bearing being positioned distal to the first bend element.

21. The medical device of claim 20, wherein the bearing is a plurality of roller bearings configured to facilitate relative rotation between the treatment member and the outer tubular member.

22. The medical device of claim 20, wherein a taper shape of the distally tapering portion of the distal-most end portion is different from a taper shape of the proximally tapering portion of the distal-most end portion.

* * * * *